(12) United States Patent
DeCarlo (10) Patent No.: US 8,506,565 B2
(45) Date of Patent: Aug. 13, 2013

(54) ELECTROSURGICAL DEVICE WITH LED ADAPTER

(75) Inventor: Arnold V. DeCarlo, Frederick, CO (US)

(73) Assignee: Covidien LP, Mansfield, MA (US)

( * ) Notice: Subject to any disclaimer, the term of this patent is extended or adjusted under 35 U.S.C. 154(b) by 1325 days.

(21) Appl. No.: 11/895,200

(22) Filed: Aug. 23, 2007

(65) Prior Publication Data

US 2009/0054890 A1    Feb. 26, 2009

(51) Int. Cl.
*A61B 18/14* (2006.01)

(52) U.S. Cl.
USPC .............................................. 606/42; 606/45

(58) Field of Classification Search
USPC .......................................... 606/41, 45, 1, 42
See application file for complete search history.

(56) References Cited

U.S. PATENT DOCUMENTS

| | | | |
|---|---|---|---|
| 2,002,594 A | 3/1933 | Wappler et al. |
| 2,031,682 A | 2/1936 | Charles et al. |
| 2,102,270 A | 12/1937 | Hyams |
| 2,196,171 A | 4/1940 | Arnesen |
| 2,993,178 A | 7/1961 | Burger |
| 3,058,470 A | 10/1962 | Seeliger et al. |
| 3,219,029 A | 11/1965 | Richards et al. |
| 3,460,539 A | 8/1969 | Anhalt, Sr. |
| 3,494,363 A | 2/1970 | Jackson |
| 3,648,001 A | 3/1972 | Anderson |
| 3,675,655 A | 7/1972 | Sittner |
| 3,699,967 A | 10/1972 | Anderson |
| 3,720,896 A | 3/1973 | Beierlein |
| 3,801,766 A | 4/1974 | Morrison, Jr. |
| 3,801,800 A | 4/1974 | Newton |
| 3,825,004 A | 7/1974 | Durden, III |
| 3,828,780 A | 8/1974 | Morrison, Jr. |
| 3,875,945 A | 4/1975 | Friedman |
| 3,902,494 A | 9/1975 | Haberlen et al. |
| 3,906,955 A | 9/1975 | Roberts |
| 3,967,084 A | 6/1976 | Pounds |
| 3,974,833 A | 8/1976 | Durden, III |
| 4,014,343 A | 3/1977 | Esty |
| 4,032,738 A | 6/1977 | Esty et al. |
| 4,034,761 A | 7/1977 | Prater et al. |

(Continued)

FOREIGN PATENT DOCUMENTS

| | | |
|---|---|---|
| DE | 24 29 021 A1 | 1/1976 |
| DE | 30 45 996 | 7/1982 |

(Continued)

OTHER PUBLICATIONS

International Search Report from PCT-US03-37111; Jul. 21, 2004.

(Continued)

*Primary Examiner* — Michael Peffley
*Assistant Examiner* — Samantha Good (57) ABSTRACT

The present disclosure includes an electrosurgical instrument which further includes a housing having distal and proximal ends. The electrosurgical instrument also includes a light-emitting diode adapter having distal and proximal ends configured to selectively engage the distal end of the housing. The light-emitting diode adapter also includes at least one light-emitting diode disposed therein. The light-emitting diode is adapted to connect to an electrosurgical energy source and being selectively activatable to emit light from the adapter. The at least one electrode is configured to selectively engage the distal end of the light-emitting diode adapter and adapted to connect to the electrosurgical energy source.

14 Claims, 6 Drawing Sheets

(56) References Cited

U.S. PATENT DOCUMENTS

| | | |
|---|---|---|
| 4,038,984 A | 8/1977 | Sittner |
| 4,112,950 A | 9/1978 | Pike |
| D253,247 S | 10/1979 | Gill |
| 4,232,676 A | 11/1980 | Herczog |
| 4,314,559 A | 2/1982 | Allen |
| 4,427,006 A | 1/1984 | Nottke |
| 4,443,935 A | 4/1984 | Zamba et al. |
| 4,459,443 A | 7/1984 | Lewandowski |
| 4,463,234 A | 7/1984 | Bennewitz |
| 4,463,759 A | 8/1984 | Garito et al. |
| 4,492,231 A | 1/1985 | Auth |
| 4,492,832 A | 1/1985 | Taylor |
| 4,545,375 A | 10/1985 | Cline |
| 4,562,838 A | 1/1986 | Walker |
| 4,589,411 A | 5/1986 | Friedman |
| 4,593,691 A | 6/1986 | Lindstrom et al. |
| 4,595,809 A | 6/1986 | Pool |
| 4,606,342 A | 8/1986 | Zamba et al. |
| 4,619,258 A | 10/1986 | Pool |
| 4,620,548 A | 11/1986 | Hasselbrack |
| 4,625,723 A | 12/1986 | Altnether et al. |
| 4,640,279 A | 2/1987 | Beard |
| 4,642,128 A | 2/1987 | Solorzano |
| 4,655,215 A | 4/1987 | Pike |
| 4,657,016 A | 4/1987 | Garito et al. |
| 4,683,884 A | 8/1987 | Hatfield et al. |
| 4,688,569 A | 8/1987 | Rabinowitz |
| 4,701,193 A | 10/1987 | Robertson et al. |
| 4,712,544 A | 12/1987 | Ensslin |
| 4,735,603 A | 4/1988 | Goodson et al. |
| 4,754,754 A | 7/1988 | Garito et al. |
| 4,785,807 A | 11/1988 | Blanch |
| 4,788,977 A | 12/1988 | Farin et al. |
| 4,794,215 A | 12/1988 | Sawada et al. |
| 4,796,623 A | 1/1989 | Krasner et al. |
| 4,803,323 A | 2/1989 | Bauer et al. |
| 4,811,733 A | 3/1989 | Borsanyi et al. |
| 4,827,911 A | 5/1989 | Broadwin et al. |
| 4,827,927 A | 5/1989 | Newton |
| D301,739 S | 6/1989 | Turner et al. |
| 4,846,790 A | 7/1989 | Hornlein et al. |
| 4,850,353 A | 7/1989 | Stasz et al. |
| 4,860,745 A | 8/1989 | Farin et al. |
| 4,862,889 A | 9/1989 | Feucht |
| 4,862,890 A | 9/1989 | Stasz et al. |
| 4,869,715 A | 9/1989 | Sherburne |
| 4,872,454 A | 10/1989 | DeOliveira et al. |
| 4,876,110 A | 10/1989 | Blanch |
| 4,886,060 A | 12/1989 | Wiksell |
| 4,901,719 A | 2/1990 | Trenconsky et al. |
| 4,903,696 A | 2/1990 | Stasz et al. |
| 4,909,249 A | 3/1990 | Akkas et al. |
| 4,911,159 A | 3/1990 | Johnson et al. |
| 4,916,275 A | 4/1990 | Almond |
| 4,919,129 A | 4/1990 | Weber, Jr. et al. |
| 4,921,476 A | 5/1990 | Wuchinich |
| 4,922,903 A | 5/1990 | Welch et al. |
| 4,931,047 A | 6/1990 | Broadwin et al. |
| 4,949,734 A | 8/1990 | Bernstein |
| 4,969,885 A | 11/1990 | Farin |
| 4,986,839 A | 1/1991 | Wertz et al. |
| 4,988,334 A | 1/1991 | Hornlein et al. |
| 5,000,754 A | 3/1991 | DeOliveira et al. |
| 5,011,483 A | 4/1991 | Sleister |
| 5,013,312 A | 5/1991 | Parins et al. |
| 5,015,227 A | 5/1991 | Broadwin et al. |
| 5,026,368 A | 6/1991 | Adair |
| 5,035,695 A | 7/1991 | Weber, Jr. et al. |
| 5,046,506 A | 9/1991 | Singer |
| 5,055,100 A | 10/1991 | Olsen |
| 5,071,418 A | 12/1991 | Rosenbaum |
| 5,074,863 A | 12/1991 | Dines |
| 5,076,276 A | 12/1991 | Sakurai et al. |
| 5,088,997 A | 2/1992 | Delahuerga et al. |
| 5,098,430 A | 3/1992 | Fleenor |
| 5,100,402 A | 3/1992 | Fan |
| 5,108,391 A | 4/1992 | Flachenecker et al. |
| 5,133,714 A | 7/1992 | Beane |
| 5,147,292 A | 9/1992 | Kullas et al. |
| D330,253 S | 10/1992 | Burek |
| 5,154,709 A | 10/1992 | Johnson |
| 5,160,334 A | 11/1992 | Billings et al. |
| 5,162,044 A | 11/1992 | Gahn et al. |
| 5,167,659 A | 12/1992 | Ohtomo et al. |
| 5,178,605 A | 1/1993 | Imonti |
| 5,190,517 A | 3/1993 | Zieve et al. |
| 5,192,267 A | 3/1993 | Shapira et al. |
| 5,195,959 A | 3/1993 | Smith |
| 5,196,007 A | 3/1993 | Ellman et al. |
| 5,197,962 A | 3/1993 | Sansom et al. |
| 5,199,944 A | 4/1993 | Cosmescu |
| 5,217,457 A | 6/1993 | Delahuerga et al. |
| 5,224,944 A | 7/1993 | Elliott |
| 5,226,904 A | 7/1993 | Gentelia et al. |
| 5,233,515 A | 8/1993 | Cosman |
| 5,234,428 A | 8/1993 | Kaufman |
| 5,234,429 A | 8/1993 | Goldhaber |
| 5,242,442 A | 9/1993 | Hirschfeld |
| 5,244,462 A | 9/1993 | Delahuerga et al. |
| 5,246,440 A | 9/1993 | Van Noord |
| 5,254,082 A | 10/1993 | Takase |
| 5,254,117 A | 10/1993 | Rigby et al. |
| 5,256,138 A | 10/1993 | Burek et al. |
| 5,261,906 A | 11/1993 | Pennino et al. |
| 5,269,781 A | 12/1993 | Hewell, III |
| 5,275,151 A | 1/1994 | Shockey et al. |
| 5,300,087 A | 4/1994 | Knoepfler |
| 5,304,763 A | 4/1994 | Ellman et al. |
| 5,306,238 A | 4/1994 | Fleenor |
| 5,312,329 A | 5/1994 | Beaty et al. |
| 5,312,400 A | 5/1994 | Bales et al. |
| 5,312,401 A | 5/1994 | Newton et al. |
| 5,318,516 A | 6/1994 | Cosmescu |
| 5,318,565 A | 6/1994 | Kuriloff et al. |
| 5,322,503 A | 6/1994 | Desai |
| 5,330,470 A | 7/1994 | Hagen |
| 5,334,183 A | 8/1994 | Wuchinich |
| 5,342,356 A | 8/1994 | Ellman et al. |
| 5,348,555 A | 9/1994 | Zinnanti |
| 5,376,089 A | 12/1994 | Smith |
| 5,380,320 A | 1/1995 | Morris |
| 5,382,247 A | 1/1995 | Cimino et al. |
| 5,395,363 A | 3/1995 | Billings et al. |
| 5,399,823 A | 3/1995 | McCusker |
| 5,401,273 A | 3/1995 | Shippert |
| 5,403,882 A | 4/1995 | Huggins |
| 5,406,945 A | 4/1995 | Riazzi et al. |
| 5,409,484 A | 4/1995 | Erlich et al. |
| 5,413,575 A | 5/1995 | Haenggi |
| 5,421,829 A | 6/1995 | Olichney et al. |
| 5,423,838 A | 6/1995 | Willard |
| 5,431,645 A | 7/1995 | Smith et al. |
| 5,431,650 A | 7/1995 | Cosmescu |
| 5,451,222 A | 9/1995 | De Maagd et al. |
| 5,460,602 A | 10/1995 | Shapira |
| 5,462,522 A | 10/1995 | Sakurai et al. |
| 5,468,240 A | 11/1995 | Gentelia et al. |
| 5,472,442 A | 12/1995 | Klicek |
| 5,472,443 A | 12/1995 | Cordis et al. |
| 5,484,398 A | 1/1996 | Stoddard |
| 5,484,434 A | 1/1996 | Cartmell et al. |
| 5,486,162 A | 1/1996 | Brumbach |
| 5,496,314 A | 3/1996 | Eggers |
| 5,498,654 A | 3/1996 | Shimasaki et al. |
| D370,731 S | 6/1996 | Corace et al. |
| 5,531,722 A | 7/1996 | Van Hale |
| 5,549,604 A | 8/1996 | Sutcu et al. |
| 5,561,278 A | 10/1996 | Rutten |
| 5,599,348 A | 2/1997 | Gentelia et al. |
| 5,601,224 A | 2/1997 | Bishop et al. |
| 5,609,573 A | 3/1997 | Sandock |
| 5,626,575 A | 5/1997 | Crenner |
| 5,630,426 A | 5/1997 | Eggers et al. |
| 5,630,812 A | 5/1997 | Ellman et al. |

| | | |
|---|---|---|
| 5,633,578 A | 5/1997 | Eggers et al. |
| 5,634,912 A | 6/1997 | Injev |
| 5,634,935 A | 6/1997 | Taheri |
| 5,643,256 A | 7/1997 | Urueta |
| D384,148 S | 9/1997 | Monson |
| 5,669,907 A | 9/1997 | Platt, Jr. et al. |
| 5,674,219 A | 10/1997 | Monson et al. |
| 5,693,044 A | 12/1997 | Cosmescu |
| 5,693,050 A | 12/1997 | Speiser |
| 5,693,052 A | 12/1997 | Weaver |
| 5,697,926 A | 12/1997 | Weaver |
| 5,702,360 A | 12/1997 | Dieras et al. |
| 5,702,387 A | 12/1997 | Arts et al. |
| 5,712,543 A | 1/1998 | Sjostrom |
| 5,713,895 A | 2/1998 | Lontine et al. |
| 5,720,745 A | 2/1998 | Farin et al. |
| D393,067 S | 3/1998 | Geary et al. |
| 5,749,869 A | 5/1998 | Lindenmeier et al. |
| 5,765,418 A | 6/1998 | Rosenberg |
| 5,776,092 A | 7/1998 | Farin et al. |
| 5,788,688 A | 8/1998 | Bauer et al. |
| 5,797,907 A | 8/1998 | Clement |
| 5,800,431 A | 9/1998 | Brown |
| 5,836,897 A | 11/1998 | Sakurai et al. |
| 5,836,909 A | 11/1998 | Cosmescu |
| 5,836,944 A | 11/1998 | Cosmescu |
| D402,030 S | 12/1998 | Roberts et al. |
| D402,031 S | 12/1998 | Roberts et al. |
| 5,843,109 A | 12/1998 | Mehta et al. |
| 5,846,236 A | 12/1998 | Lindenmeier et al. |
| 5,859,527 A | 1/1999 | Cook |
| 5,868,768 A | 2/1999 | Wicherski et al. |
| 5,876,400 A | 3/1999 | Songer |
| 5,888,200 A | 3/1999 | Walen |
| 5,893,848 A | 4/1999 | Negus et al. |
| 5,893,849 A | 4/1999 | Weaver |
| 5,893,862 A | 4/1999 | Pratt et al. |
| 5,913,864 A | 6/1999 | Garito et al. |
| 5,919,219 A | 7/1999 | Knowlton |
| 5,928,159 A | 7/1999 | Eggers et al. |
| 5,938,589 A | 8/1999 | Wako et al. |
| 5,941,887 A | 8/1999 | Steen et al. |
| 5,944,737 A | 8/1999 | Tsonton et al. |
| 5,951,548 A | 9/1999 | DeSisto et al. |
| 5,951,581 A | 9/1999 | Saadat et al. |
| 5,954,686 A | 9/1999 | Garito et al. |
| 5,972,007 A | 10/1999 | Sheffield et al. |
| 6,004,318 A | 12/1999 | Garito et al. |
| 6,004,333 A | 12/1999 | Sheffield et al. |
| 6,004,335 A | 12/1999 | Vaitekunas et al. |
| 6,010,499 A | 1/2000 | Cobb |
| 6,022,347 A | 2/2000 | Lindenmeier et al. |
| 6,045,564 A | 4/2000 | Walen |
| 6,063,050 A | 5/2000 | Manna et al. |
| 6,068,603 A | 5/2000 | Suzuki |
| 6,068,627 A | 5/2000 | Orszulak et al. |
| 6,070,444 A | 6/2000 | Lontine et al. |
| 6,071,281 A | 6/2000 | Burnside et al. |
| 6,074,386 A | 6/2000 | Goble et al. |
| 6,074,387 A | 6/2000 | Heim et al. |
| 6,086,544 A | 7/2000 | Hibner et al. |
| 6,090,123 A | 7/2000 | Culp et al. |
| 6,099,525 A | 8/2000 | Cosmescu |
| 6,117,134 A | 9/2000 | Cunningham et al. |
| 6,139,547 A | 10/2000 | Lontine et al. |
| D433,752 S | 11/2000 | Saravia |
| 6,142,995 A | 11/2000 | Cosmescu |
| 6,146,353 A | 11/2000 | Platt, Jr. |
| 6,149,648 A | 11/2000 | Cosmescu |
| 6,156,035 A | 12/2000 | Songer |
| 6,197,024 B1 | 3/2001 | Sullivan |
| 6,200,311 B1 | 3/2001 | Danek et al. |
| D441,077 S | 4/2001 | Garito et al. |
| 6,213,999 B1 | 4/2001 | Platt, Jr. et al. |
| 6,214,003 B1 | 4/2001 | Morgan et al. |
| 6,238,388 B1 | 5/2001 | Ellman et al. |
| 6,241,723 B1 | 6/2001 | Heim et al. |
| 6,241,753 B1 | 6/2001 | Knowlton |
| 6,249,706 B1 | 6/2001 | Sobota et al. |
| 6,251,110 B1 | 6/2001 | Wampler |
| 6,257,241 B1 | 7/2001 | Wampler |
| 6,258,088 B1 | 7/2001 | Tzonev et al. |
| 6,273,862 B1 | 8/2001 | Privitera et al. |
| 6,277,083 B1 | 8/2001 | Eggers et al. |
| 6,287,305 B1 | 9/2001 | Heim et al. |
| 6,287,344 B1 | 9/2001 | Wampler et al. |
| 6,312,441 B1 | 11/2001 | Deng |
| 6,325,799 B1 | 12/2001 | Goble |
| D453,222 S | 1/2002 | Garito et al. |
| D453,833 S | 2/2002 | Hess |
| 6,350,276 B1 | 2/2002 | Knowlton |
| 6,352,544 B1 | 3/2002 | Spitz |
| 6,355,034 B2 | 3/2002 | Cosmescu |
| 6,358,281 B1 | 3/2002 | Berrang et al. |
| 6,361,532 B1 | 3/2002 | Burek |
| D457,955 S | 5/2002 | Bilitz |
| 6,395,001 B1 | 5/2002 | Ellman et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,725 B1 | 6/2002 | Khandkar et al. |
| 6,413,255 B1 | 7/2002 | Stern |
| 6,416,491 B1 | 7/2002 | Edwards et al. |
| 6,416,509 B1 | 7/2002 | Goble et al. |
| 6,425,912 B1 | 7/2002 | Knowlton |
| 6,458,078 B1 | 10/2002 | Ludtke et al. |
| 6,458,122 B1 | 10/2002 | Pozzato |
| 6,458,125 B1 | 10/2002 | Cosmescu |
| 6,461,352 B2 | 10/2002 | Morgan et al. |
| 6,464,702 B2 | 10/2002 | Schulze et al. |
| 6,471,659 B2 | 10/2002 | Eggers et al. |
| 6,494,882 B1 | 12/2002 | Lebouitz et al. |
| 6,500,169 B1 | 12/2002 | Deng |
| 6,511,479 B2 | 1/2003 | Gentelia et al. |
| 6,526,320 B2 | 2/2003 | Mitchell |
| 6,551,313 B1 | 4/2003 | Levin |
| 6,558,383 B2 | 5/2003 | Cunningham et al. |
| 6,585,664 B2 | 7/2003 | Burdorff et al. |
| 6,589,239 B2 | 7/2003 | Khandkar et al. |
| 6,610,054 B1 | 8/2003 | Edwards et al. |
| 6,610,057 B1 | 8/2003 | Ellman et al. |
| 6,616,658 B2 | 9/2003 | Ineson |
| 6,618,626 B2 | 9/2003 | West, Jr. et al. |
| 6,620,161 B2 | 9/2003 | Schulze et al. |
| 6,632,193 B1 | 10/2003 | Davison et al. |
| 6,652,514 B2 | 11/2003 | Ellman et al. |
| 6,662,053 B2 | 12/2003 | Borkan |
| 6,669,691 B1 | 12/2003 | Taimisto |
| 6,685,701 B2 | 2/2004 | Orszulak et al. |
| 6,685,704 B2 | 2/2004 | Greep |
| 6,702,812 B2 | 3/2004 | Cosmescu |
| 6,712,813 B2 | 3/2004 | Ellman et al. |
| 6,740,079 B1 | 5/2004 | Eggers et al. |
| 6,747,218 B2 | 6/2004 | Huseman et al. |
| D493,530 S | 7/2004 | Reschke |
| D493,888 S | 8/2004 | Reschke |
| D494,270 S | 8/2004 | Reschke |
| D495,051 S | 8/2004 | Reschke |
| D495,052 S | 8/2004 | Reschke |
| 6,794,929 B2 | 9/2004 | Pelly |
| 6,830,569 B2 | 12/2004 | Thompson et al. |
| 6,840,948 B2 | 1/2005 | Albrecht et al. |
| 6,855,140 B2 | 2/2005 | Albrecht et al. |
| 6,902,536 B2 | 6/2005 | Manna et al. |
| 6,905,496 B2 | 6/2005 | Ellman et al. |
| 6,923,804 B2 | 8/2005 | Eggers et al. |
| 6,923,809 B2 | 8/2005 | Eggers et al. |
| 6,939,347 B2 | 9/2005 | Thompson |
| 6,955,674 B2 | 10/2005 | Eick et al. |
| D515,412 S | 2/2006 | Waaler et al. |
| D521,641 S | 5/2006 | Reschke et al. |
| D535,396 S | 1/2007 | Reschke et al. |
| 7,156,842 B2 | 1/2007 | Sartor et al. |
| 7,156,844 B2 | 1/2007 | Reschke et al. |
| 7,178,941 B2 | 2/2007 | Roberge et al. |
| 7,235,072 B2 | 6/2007 | Sartor et al. |
| 7,241,294 B2 | 7/2007 | Reschke |

| | | |
|---|---|---|
| 7,244,257 B2 | 7/2007 | Podhajsky et al. |
| 2001/0047183 A1 | 11/2001 | Privitera et al. |
| 2001/0049524 A1 | 12/2001 | Morgan et al. |
| 2002/0019596 A1 | 2/2002 | Eggers et al. |
| 2002/0019631 A1 | 2/2002 | Kidder et al. |
| 2002/0022838 A1 | 2/2002 | Cunningham et al. |
| 2002/0026145 A1 | 2/2002 | Bagaoisan et al. |
| 2002/0029032 A1 | 3/2002 | Arkin |
| 2002/0035364 A1 | 3/2002 | Schoenman et al. |
| 2002/0049427 A1 | 4/2002 | Wiener et al. |
| 2002/0058931 A1* | 5/2002 | Parker et al. .................... 606/16 |
| 2002/0058958 A1 | 5/2002 | Walen |
| 2002/0087179 A1 | 7/2002 | Culp et al. |
| 2002/0095199 A1 | 7/2002 | West, Jr. et al. |
| 2002/0103485 A1 | 8/2002 | Melnyk et al. |
| 2002/0107517 A1 | 8/2002 | Witt et al. |
| 2002/0111622 A1 | 8/2002 | Khandkar et al. |
| 2002/0133148 A1 | 9/2002 | Daniel et al. |
| 2002/0151886 A1 | 10/2002 | Wood |
| 2002/0151887 A1 | 10/2002 | Stern et al. |
| 2002/0156471 A1 | 10/2002 | Stern et al. |
| 2002/0173776 A1 | 11/2002 | Batchelor et al. |
| 2002/0198519 A1 | 12/2002 | Qin et al. |
| 2003/0004508 A1 | 1/2003 | Morgan et al. |
| 2003/0014043 A1 | 1/2003 | Henry et al. |
| 2003/0032950 A1 | 2/2003 | Altshuler et al. |
| 2003/0050633 A1 | 3/2003 | Ellman et al. |
| 2003/0055421 A1 | 3/2003 | West et al. |
| 2003/0065321 A1 | 4/2003 | Carmel et al. |
| 2003/0078572 A1 | 4/2003 | Pearson et al. |
| 2003/0083655 A1 | 5/2003 | Van Wyk |
| 2003/0088247 A1 | 5/2003 | Ineson |
| 2003/0095781 A1 | 5/2003 | Williams |
| 2003/0109864 A1 | 6/2003 | Greep et al. |
| 2003/0109865 A1 | 6/2003 | Greep et al. |
| 2003/0130663 A1 | 7/2003 | Walen |
| 2003/0144680 A1 | 7/2003 | Kellogg et al. |
| 2003/0163125 A1 | 8/2003 | Greep |
| 2003/0199856 A1 | 10/2003 | Hill et al. |
| 2003/0199866 A1 | 10/2003 | Stern et al. |
| 2003/0199869 A1 | 10/2003 | Johnson et al. |
| 2003/0212393 A1 | 11/2003 | Knowlton et al. |
| 2003/0212397 A1 | 11/2003 | Avrahami et al. |
| 2003/0216728 A1 | 11/2003 | Stern et al. |
| 2003/0220635 A1 | 11/2003 | Knowlton et al. |
| 2003/0220638 A1 | 11/2003 | Metzger |
| 2003/0225401 A1 | 12/2003 | Eggers et al. |
| 2003/0229341 A1 | 12/2003 | Albrecht et al. |
| 2003/0229343 A1 | 12/2003 | Albrecht et al. |
| 2004/0000316 A1 | 1/2004 | Knowlton et al. |
| 2004/0002704 A1 | 1/2004 | Knowlton et al. |
| 2004/0002705 A1 | 1/2004 | Knowlton et al. |
| 2004/0010246 A1 | 1/2004 | Takahashi |
| 2004/0015160 A1 | 1/2004 | Lovewell |
| 2004/0015161 A1 | 1/2004 | Lovewell |
| 2004/0015162 A1 | 1/2004 | McGaffigan |
| 2004/0015216 A1 | 1/2004 | DeSisto |
| 2004/0024395 A1 | 2/2004 | Ellman et al. |
| 2004/0024396 A1 | 2/2004 | Eggers |
| 2004/0030328 A1 | 2/2004 | Eggers et al. |
| 2004/0030330 A1 | 2/2004 | Brassell et al. |
| 2004/0030332 A1 | 2/2004 | Knowlton et al. |
| 2004/0034346 A1 | 2/2004 | Stern et al. |
| 2004/0054370 A1 | 3/2004 | Given |
| 2004/0097916 A1* | 5/2004 | Thompson et al. ............. 606/34 |
| 2004/0111087 A1 | 6/2004 | Stern et al. |
| 2004/0124964 A1 | 7/2004 | Wang et al. |
| 2004/0127889 A1 | 7/2004 | Zhang et al. |
| 2004/0143677 A1 | 7/2004 | Novak |
| 2004/0147909 A1 | 7/2004 | Johnston et al. |
| 2004/0162553 A1 | 8/2004 | Peng et al. |
| 2004/0167512 A1 | 8/2004 | Stoddard et al. |
| 2004/0172011 A1 | 9/2004 | Wang et al. |
| 2004/0172015 A1 | 9/2004 | Novak |
| 2004/0172016 A1 | 9/2004 | Bek et al. |
| 2004/0181140 A1 | 9/2004 | Falwell et al. |
| 2004/0236323 A1 | 11/2004 | Schoenman et al. |
| 2004/0243120 A1 | 12/2004 | Orszulak et al. |
| 2004/0267252 A1 | 12/2004 | Washington et al. |
| 2004/0267254 A1 | 12/2004 | Manzo et al. |
| 2004/0267297 A1 | 12/2004 | Malackowski |
| 2005/0033286 A1 | 2/2005 | Eggers et al. |
| 2005/0059858 A1 | 3/2005 | Frith et al. |
| 2005/0059967 A1 | 3/2005 | Breazeale, Jr. et al. |
| 2005/0065510 A1 | 3/2005 | Carmel et al. |
| 2005/0070891 A1 | 3/2005 | DeSisto |
| 2005/0085804 A1 | 4/2005 | McGaffigan |
| 2005/0096645 A1 | 5/2005 | Wellman et al. |
| 2005/0096646 A1 | 5/2005 | Wellman et al. |
| 2005/0096681 A1 | 5/2005 | Desinger et al. |
| 2005/0113817 A1 | 5/2005 | Isaacson et al. |
| 2005/0113818 A1 | 5/2005 | Sartor et al. |
| 2005/0113824 A1 | 5/2005 | Sartor et al. |
| 2005/0113825 A1 | 5/2005 | Cosmescu |
| 2005/0149001 A1 | 7/2005 | Uchikubo et al. |
| 2005/0154385 A1 | 7/2005 | Heim et al. |
| 2006/0041257 A1 | 2/2006 | Sartor et al. |
| 2006/0058783 A1 | 3/2006 | Buchman |
| 2006/0069386 A1 | 3/2006 | Dubnack et al. |
| 2006/0178667 A1 | 8/2006 | Sartor et al. |
| 2006/0224045 A1 | 10/2006 | Whipple et al. |
| 2006/0241577 A1 | 10/2006 | Balbierz et al. |
| 2006/0282072 A1 | 12/2006 | DesRosier |
| 2007/0049926 A1 | 3/2007 | Sartor |
| 2007/0049927 A1 | 3/2007 | Saltzman |
| 2007/0093810 A1 | 4/2007 | Sartor |
| 2007/0142832 A1 | 6/2007 | Sartor |
| 2007/0167943 A1 | 7/2007 | Janssen et al. |

FOREIGN PATENT DOCUMENTS

| | | |
|---|---|---|
| DE | 202004002963 | 4/2004 |
| EP | 1050277 | 11/2000 |
| EP | 1050279 | 11/2000 |
| EP | 1082945 | 3/2001 |
| EP | 1278007 | 1/2003 |
| EP | 1293171 | 3/2003 |
| EP | 1402837 | 3/2004 |
| EP | 1656900 | 5/2006 |
| EP | 1693021 | 8/2006 |
| EP | 1645234 | 12/2006 |
| FR | 2235669 | 1/1975 |
| WO | WO 94/20032 | 9/1994 |
| WO | WO 96/39086 | 12/1996 |
| WO | WO 98/43264 | 10/1998 |
| WO | WO 01/64122 | 9/2001 |
| WO | WO 02/47568 A1 | 6/2002 |
| WO | WO 2004/010883 A1 | 2/2004 |
| WO | WO 2004/045436 A1 | 6/2004 |
| WO | WO 2004054626 | 7/2004 |
| WO | WO 2004/073753 A2 | 9/2004 |
| WO | WO 2005/060849 A1 | 7/2005 |

OTHER PUBLICATIONS

International Search Report from PCT-US04-04685; Aug. 6, 2004.
International Search Report from EP-0401-5980; Sep. 30, 2004.
International Search Report from PCT-US03-22900; Nov. 20, 2003.
International Search Report from EP 05019882.9 dated Feb. 16, 2006.
International Search Report from EP 05021777.7 dated Feb. 23, 2006.
International Search Report from EP 06014461.5 dated Oct. 31, 2006.
International Search Report from EP 08014842.2 dated Nov. 20, 2008.

* cited by examiner

ELECTROSURGICAL DEVICE WITH LED ADAPTER

BACKGROUND

1. Technical Field

The present disclosure relates generally to electrosurgical instruments and, more particularly, to electrosurgical instruments with an light-emitting diode (LED) adapter.

2. Background of Related Art

Electrosurgical instruments have become widely used by surgeons in recent years. Accordingly, a need has developed for equipment and instruments which are easy to handle, are reliable and are safe in an operating environment. By and large, most electrosurgical instruments are hand-held instruments, e.g., an electrosurgical pencil, which transfer radio-frequency (RF) electrical or electrosurgical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical cutting and fulguration.

As used herein the term "electrosurgical pencil" is intended to include instruments which have a handpiece which is attached to an active electrode and which is used to cauterize, coagulate and/or cut tissue. Typically, the electrosurgical pencil may be operated by a handswitch or a foot switch. The active electrode is an electrically conducting element which is usually elongated and may be in the form of a thin flat blade with a pointed or rounded distal end. Alternatively, the active electrode may include an elongated narrow cylindrical needle which is solid or hollow with a flat, rounded, pointed or slanted distal end. Typically electrodes of this sort are known in the art as "blade", "loop", "snare", "needle" or "ball" electrodes.

Since electrosurgery requires controlled application of radio frequency energy to an operative tissue site, it is important that the surgical site is substantially illuminated for the surgeon to operate. Due to the variety of electrosurgical instruments and various types of electrodes, it is difficult for a surgeon to simply add a light source to an instrument.

SUMMARY

The present disclosure includes an electrosurgical instrument which includes a housing having distal and proximal ends. The electrosurgical instrument also includes a light-emitting diode adapter having distal and proximal ends configured to selectively engage the distal end of the housing. The light-emitting diode adapter includes at least one light-emitting diode disposed therein. The light-emitting diode is adapted to connect to an electrosurgical energy source and is being selectively activatable to emit light from the adapter. The at least one electrode is configured to selectively engage the distal end of the light-emitting diode adapter and adapted to connect to the electrosurgical energy source.

Another embodiment of the present disclosure includes an electrosurgical instrument which includes a housing having distal and proximal ends. The electrosurgical instrument also includes a light-emitting diode adapter having distal and proximal ends configured to selectively engage the distal end of the housing. The light-emitting diode adapter includes at least one light-emitting diode disposed therein and the light-emitting diode adapted to connect to an electrosurgical energy source. The light-emitting diode is selectively activatable to emit light from the light-emitting diode adapter. Also, the electrosurgical instrument includes at least one electrode configured to selectively engage to the distal end of light-emitting diode adapter. The electrode is adapted to connect to the electrosurgical energy source. The electrosurgical instrument also includes at least one switch for selectively activating at least one of the light-emitting diode and the electrode.

Still another embodiment of the present disclosure includes a light-emitting diode adapter having a housing with distal and proximal ends. The light-emitting diode is disposed at a distal end thereof. The light-emitting diode is connected to an electrosurgical energy source and is selectively activatable to emit light therefrom. An opening is defined at the distal end of the light-emitting diode adapter and is configured to receive an electrode for treating tissue. The light-emitting diode adapter also includes a mechanical interface that is configured to engage an electrosurgical instrument and connect to an electrosurgical energy source.

Still yet another embodiment of the present disclosure relates to an electrosurgical system having an electrosurgical generator which is adapted to supply electrosurgical energy to one or more electrosurgical instruments selectively connectable thereto. The electrosurgical instrument includes a housing having distal and proximal ends and a light-emitting diode adapter. The light-emitting diode adapter has distal and proximal ends and is configured to selectively engage the distal end of the housing. The light-emitting diode adapter also includes at least one light-emitting diode disposed therein and connects to an electrosurgical energy source. The light-emitting diode is selectively activatable to emit light from the adapter. At least one electrode configured to selectively engage the distal end of the light-emitting diode adapter and connects to the electrosurgical energy source.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

DETAILED DESCRIPTION

The embodiments of the presently disclosed electrosurgical pencil are described in detail with reference to the drawing figures wherein like reference numerals identify similar or identical elements. As used herein, the term "distal" refers to that portion which is further from the user while the term "proximal" refers to that portion which is closer to the user or surgeon.

Figure 1:
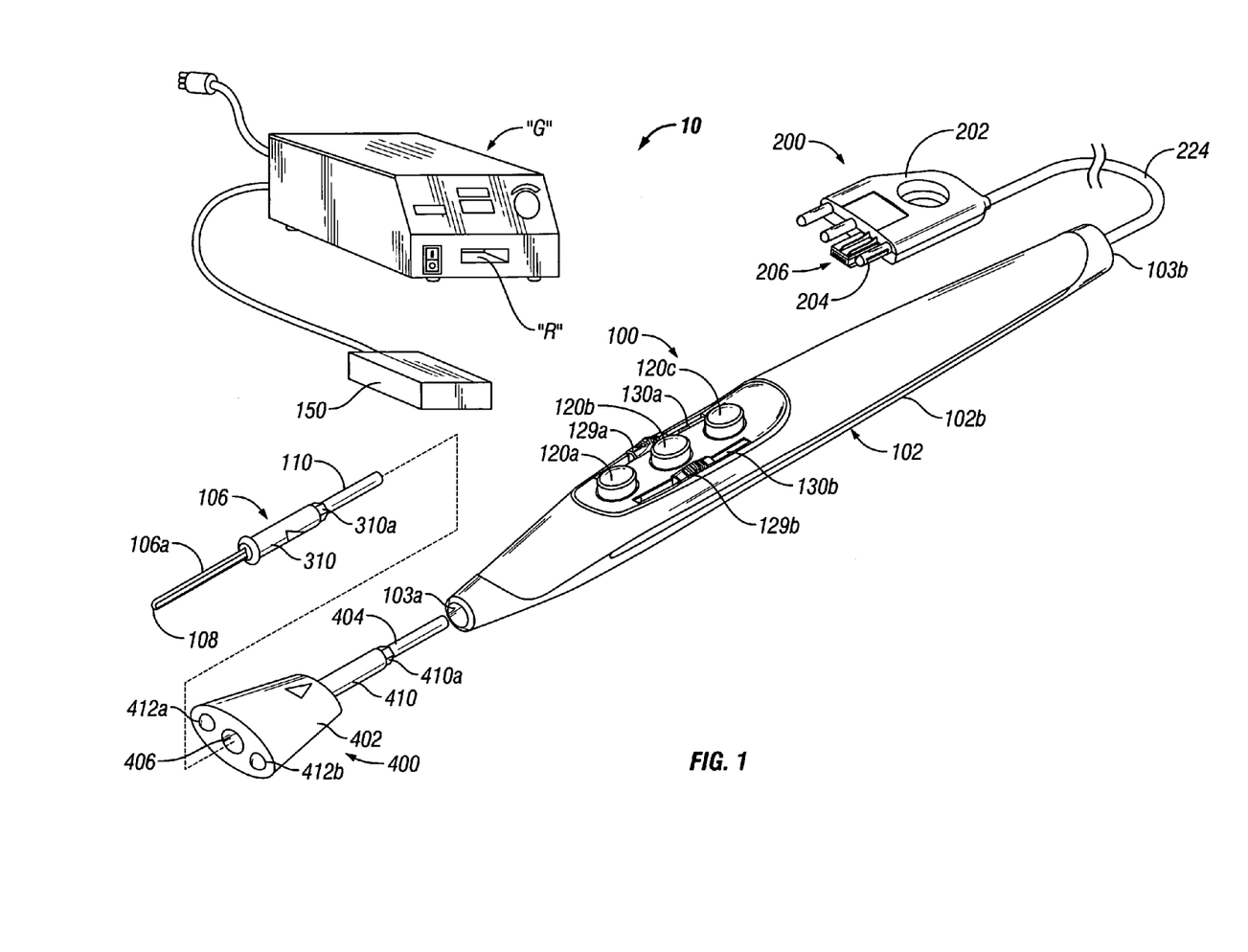
FIG. 1 is a perspective view of an electrosurgical system including an electrode, an LED adapter, and an electrosurgical pencil in accordance with an embodiment of the present disclosure.

FIG. 1 sets forth a perspective view of an electrosurgical system 10 including an electrosurgical pencil 100 constructed in accordance with one embodiment of the present disclosure. While the following description will be directed towards electrosurgical pencils it is envisioned that the features and concepts (or portions thereof) of the present disclosure can be applied to any electrosurgical type instrument, e.g., forceps, suction coagulators, vessel sealers, wands, etc.

Further, while the following description will be directed towards light-emitting diodes (LEDs) it is envisioned that the features and concepts (or portions thereof) of the present disclosure can be applied to any suitable light source, e.g., fiber optic lighting, laser, infrared, ultraviolet, fluorescent bulbs, incandescent bulbs, ambient light, etc.

As seen in FIG. 1, electrosurgical pencil 100 includes an elongated housing 102 having a top-half shell portion 102a and a bottom-half shell portion 102b. Housing 102 includes an opening 103a defined at a distal end thereof and an opening 103a defined at a proximal end thereof. A electrocautery blade 106 or an LED adapter 400 is selectively engageable with the distal opening 103a as explained in more detail below.

A cable 224 is received through opening 103b and connects to a coupling interface 300 to supply energy to distal end 103a. The proximal end of the cable 224 includes a plug 200 which operatively couples to a electrosurgical generator "G". Top-half shell portion 102a and bottom-half shell portion 102b may be bonded together using methods known by those skilled in the art, e.g., sonic energy, adhesives, snap-fit assemblies, etc. Electrosurgical pencil 100 and the intercooperating relationships of the various components contained are explained in greater detail in U.S. Publication No. 2006/0178667, the entire reference being hereby incorporated herein.

Figure 3:
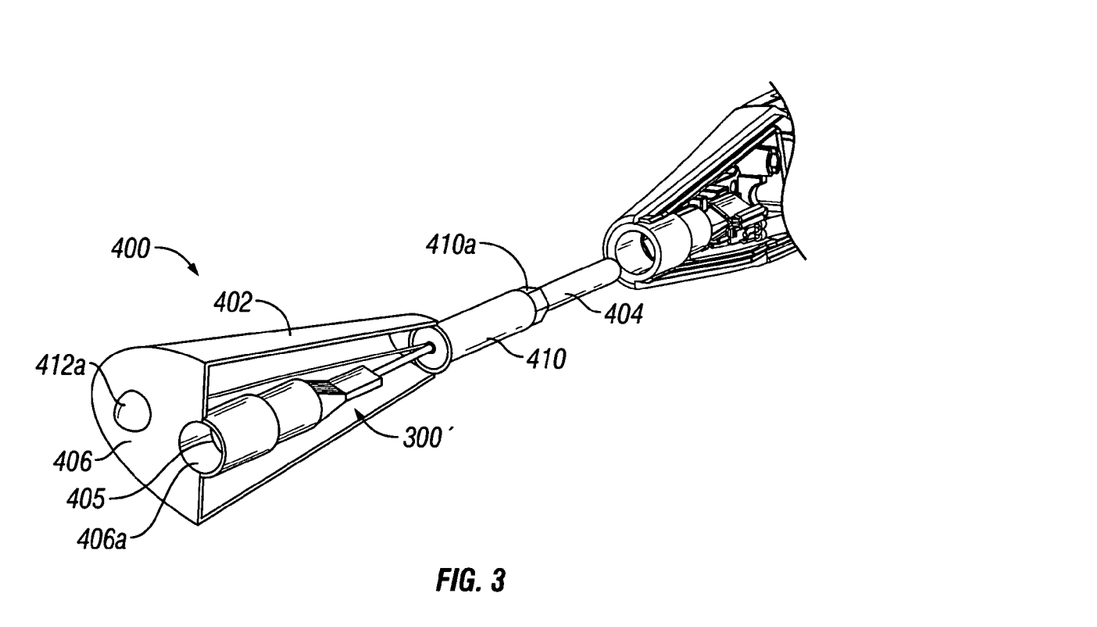
FIG. 3 is a partial, internal perspective view of a distal end of an LED adapter, in accordance with an embodiment of the present disclosure.
Figure 4:
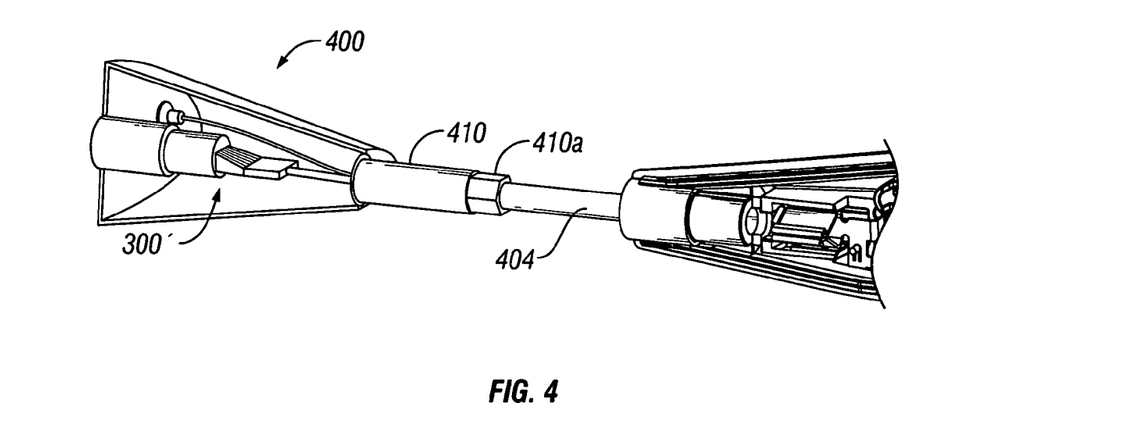
FIG. 4 is a partial, side view of the distal end of an LED adapter, in accordance with the embodiment of the FIG. 3 of the present disclosure.

Electrosurgical system 10 further includes a light-emitting diode (LED) adapter 400 having a distal end 406 and a proximal end 404 configured to selectively engage distal end opening 103a of electrosurgical pencil 100. LED adapter 400 includes a coupling interface 300' that selectively engages electrode 106 similar to coupling interface 300 described below with respect to pencil 100. FIGS. 3 and 4 depict coupling interface 300' which is described in detail further below.

LED adapter 400 includes at least one LED 412a, that is disposed on housing 402 of LED adapter 400. LED adapter 400 is adapted to connect to an electrosurgical energy source, for example, an electrosurgical generator "G". LED adapter 400 is selectively activatable to emit light when at least one of a series of switches 120a, 120b and 120c disposed on pencil 100 is actuated.

Figure 2:
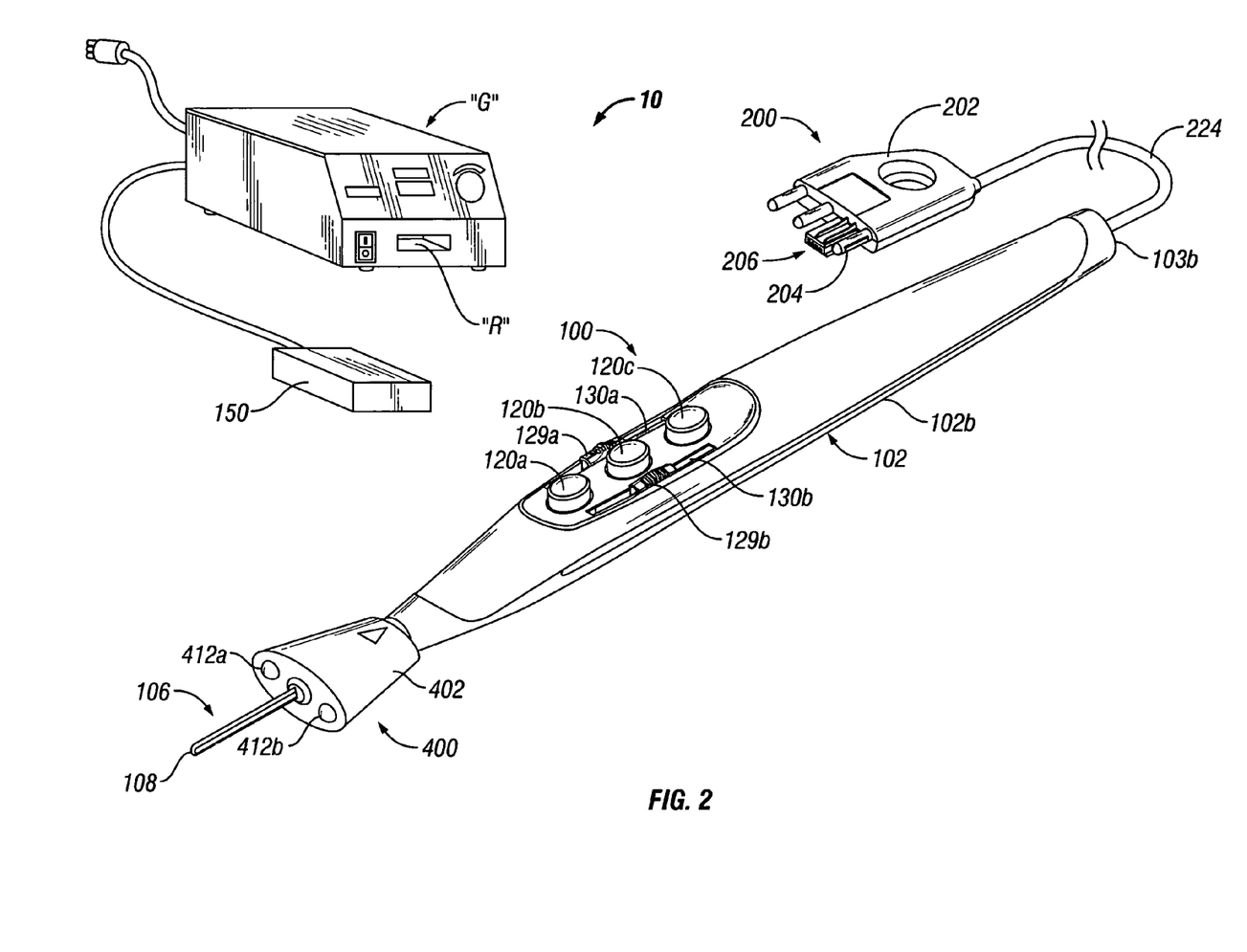
FIG. 2 is a perspective view of the electrosurgical system of FIG. 1 showing the electrode, LED adapter, and electrosurgical pencil connected for operation in accordance with the present disclosure.
Figure 5:
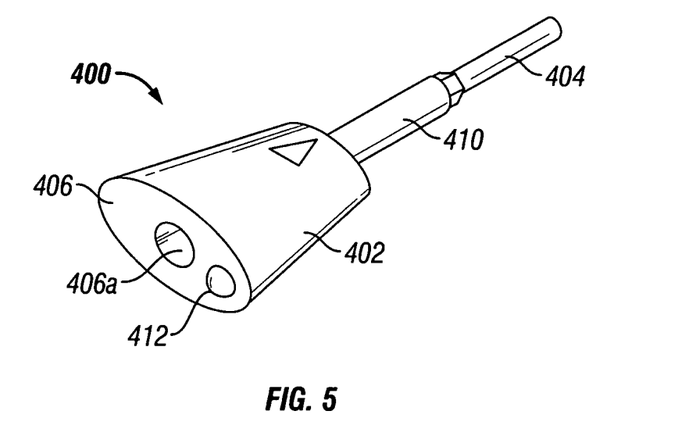
FIG. 5 is a perspective view of another embodiment of the LED adapter of the present disclosure having a single LED.

FIGS. 1 and 2 also illustrate a plurality of LEDs 412a and 412b disposed on the distal end of LED adapter 400. Also depicted in FIG. 2, the components of LED adapter 400 may also include a single LED, e.g., LED 412a on the distal end of housing 402, as depicted in FIG. 5.

Turning now to FIG. 3, a coupling interface 300' may be housed within LED adapter 400. More particularly, coupling interface 300' defines an open distal end 406a for selectively receiving proximal end 110 of an electrode 106 therein. Open distal end 406a defines a generally non-circular inner profile 405, such as, for example, ovular, triangular, rectangular, hexagonal, toothed, multi-faceted and the like, to facilitate engagement of electrode 106 therein.

More particularly, proximal end 110 of electrode 106 is supported by a collar 310 positioned between distal end 108 and proximal end 110 of electrode 106. Turning back to FIG. 1, collar 310 has a shaped outer surface 310a configured and dimensioned to complement the inner profile 405 of open distal end 406a at housing 402. In one embodiment, the open distal end 406a of housing 402 defines a hexagonal inner profile 405, as shown in FIG. 3, and collar 310 defines a hexagonal outer surface 310a.

It is envisioned that the shaped inner profile 405 of open distal end 406a of housing 302 may be formed using plastic injection molding, insert molding and/or broaching techniques.

In the same manner, proximal end 404 of LED adapter 400 may be selectively connected to distal opening 103a of electrosurgical pencil 100. More particularly, proximal end 404 of LED adapter 400 includes an outer shaped profile which is selectively engageable with open distal end 103a of electrosurgical pencil 100. For example, distal end 103a defines a non-circular inner profile (not shown), such as, for example, ovular, triangular, rectangular, hexagonal, toothed, multi-faceted and the like. A substantially similar coupling interface, as described above, is explained in greater detail in U.S. Publication No. 2006/0178667, which is incorporated in its entirety by reference herein.

As illustrated in FIGS. 3 and 4, the proximal end of LED adapter 400 includes collar 410 positioned between distal end 406 and proximal end 404 of LED adapter 400. Collar 410 has a shaped outer surface 410a configured and dimensioned to complement the inner profile 405 of open distal end 103a. More particularly, the proximal end 404 of LED adapter 400 includes a profile which matingly engages the distal end 103c of pencil 100. It is envisioned that the proximal end 404 and collar 410a of LED adapter 400 includes the same shape and configuration as the proximal end 108 and collar 310 of the electrode 106. As can be appreciated, this enables a surgeon to quickly and easily substitute LED adapter 400 into the distal end 103a of pencil 100 and re-engage the electrode 106 with the LED adapter 400. In one embodiment, the open distal end 103a of housing 102 includes a coupling interface 300 having a hexagonal profile and collar 410 defines a hexagonal outer surface 410a which mates with interface 300.

Turning now to FIG. 4, LED adapter 400 may include a stabilizer 320 disposed within its respective housing 402 in order to eliminate mechanical play in the connection of electrocautery blade 106 to housing 402. Stabilizer 320 functions to improve the retention forces of proximal end 110 in housing 402 and is typically positioned proximal to an electrocautery blade mount 322 provided near the distal end of housing 402, and coupling interface 300'.

Electrode 106, LED adapter 400 and electrosurgical pencil 100 are selectively electrically connected to convey RF energy supplied from electrosurgical generator "G", to LED adapter 400, and further to electrode 106.

Electrode 106 is configured to selectively engage to the distal end 406 of LED adapter 400 for treating tissue. LED, in turn, is configured to selectively engage the distal end of electrosurgical pencil 100, which in turn, is adapted to connect to electrosurgical generator "G" via plug 200. Plug 200 includes a housing portion 202, a controller terminal 215, and a connecting wire 224 electrically interconnecting housing portion 202 and control terminal 215. Housing portion 202 is configured and adapted to retain a common power pin 204 and a plurality of electrical contacts 206 therebetween. Plug assembly 200 and its components are explained in greater detail in U.S. Publication No. 2006/0178667, the entirety of which is incorporated by reference herein.

Electrosurgical pencil 100 includes at least one activation switches 120a-120c, each of which extends through top-half shell portion 102a of housing 102. Each activation switch 120a-120c is operatively supported on a respective tactile element 122a-122c (here shown as a snap-dome switch) provided on a switch plate 124. Each activation switch 120a-120c controls a particular amount of RF electrical energy supplied from generator "G" to LED adapter 400, which in turn, supplies energy to electrosurgical blade 106.

As seen throughout FIGS. 1 and 2, electrosurgical pencil 100 further includes an intensity controller 128 slidingly supported on or in housing 102. Intensity controller 128 includes a pair of nubs 129a, 129b which are slidingly supported, one each, in respective guide channels 130a, 130b, formed in top-half shell portion 102a of housing 102. Guide channels 130a, 130b are formed on either side of activations switches 120a-120c. By providing nubs 129a, 129b on either side of activation switches 120a-120c, intensity controller 128 can be easily manipulated by either hand of the user or the same electrosurgical pencil can be operated by a right-handed or a left-handed user.

It is envisioned that any one of switches 120a-120c and intensity controller 128 may be utilized to selectively activate LEDs 412a, 412b disposed on distal end 406 of LED adapter 400 and/or electrode 106. In use, when a surgeon activates any one of the aforementioned switches 120a-120c, LEDs 412a and 412b may illuminate on LED adapter 400. Alternatively, a separate switch may be configured to be mounted on the electrosurgical pencil 100 and/or LED adapter 400. In another embodiment, LED adapter 400 may have an independent power switch that simply powers on the LED adapter so that LEDs 412a and 412b can be selectively illuminated.

In operation, and depending on the particular electrosurgical function desired, the surgeon depresses one of activation switches 120a-120c thereby transmitting a respective characteristic signal to electrosurgical generator "G". For example, the surgeon can depress activation switch 120a to perform a cutting and/or "dissecting" function, activation switch 120b to perform a "blending" function, or activation switch 120c to perform a "hemostatic" function. In turn, generator "G" transmits an appropriate waveform output to LED adapter 400, which further transmits the appropriate waveform to electrocautery blade 106 via an internal RF line contained within housing 402 (not shown).

It is envisioned that electrosurgical pencil 100 may contain a switch, which may be any switch 120a-120c, that simultaneously activates LED 412a, 412b, and electrode 106. It is also envisioned that LED 412a, 412b and/or electrode may also be activatable by a footswitch 150.

Figure 6:
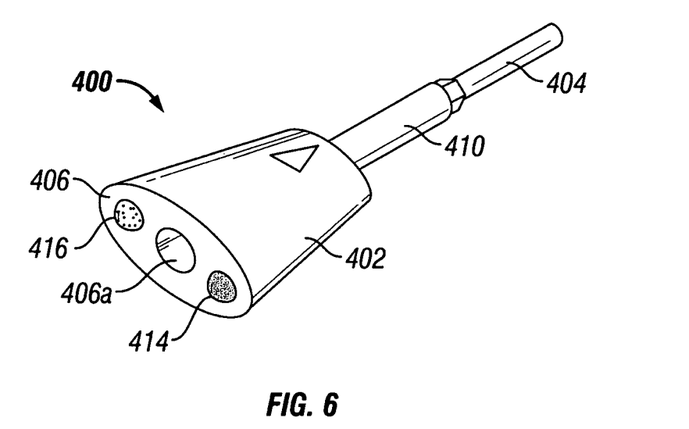
FIG. 6 is a perspective view of still another embodiment of the LED adapter of the present disclosure having at least one LED which emits a color.

As illustrated in FIG. 6, LED adapter 400, which includes LEDs 414 and 416, may be configured to emit at least one color, for example, a red color, blue color, or any suitable color, relating to a surgical condition. Further, LEDs 414 and 416, individually and/or in combination thereof, may emit a particular color depending on the operating status of electrosurgical instrument 100. Further, LEDs 414 and 416, individually and/or in combination thereof, may emit a color in order to designate that the instrument has malfunctioned. Still further LED adapter 400 may be configured to have LEDs 414 and 416 display a suitable color to designate a specific function and/or completion of a treatment.

Figure 7:
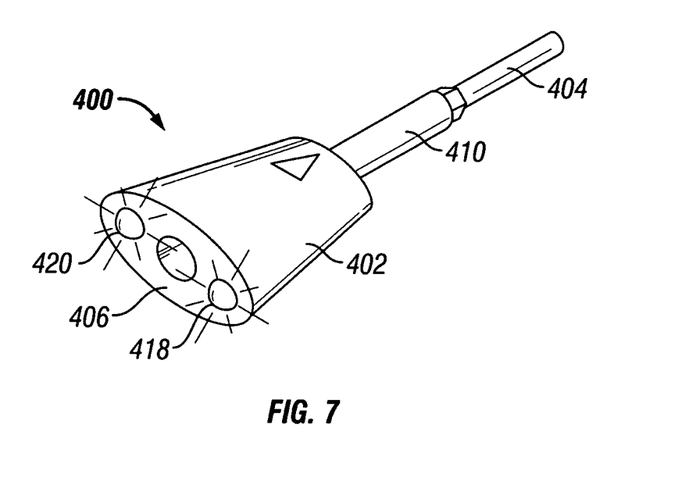
FIG. 7 is a perspective view of still another further embodiment of the LED adapter of the present disclosure having at least one LED which emits an intermittent pattern.
Figure 8:
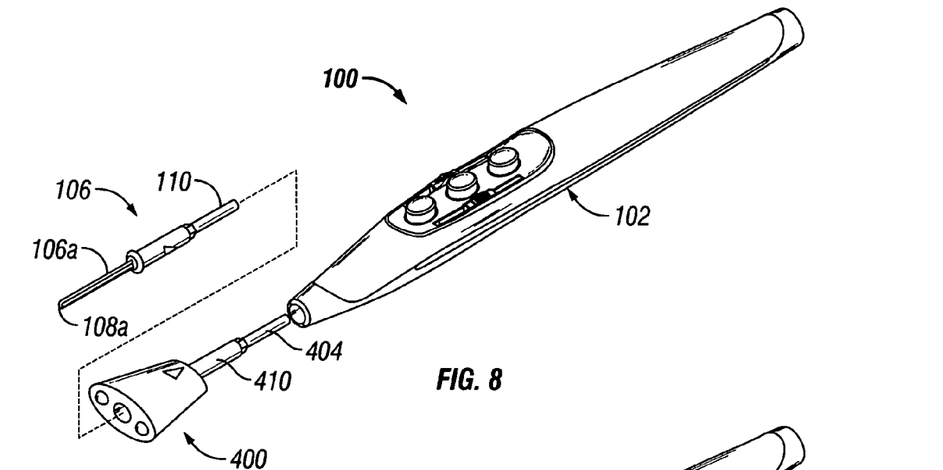
FIG. 8 is a perspective view of the electrosurgical pencil, LED adapter, and a blade electrode.
Figure 9:
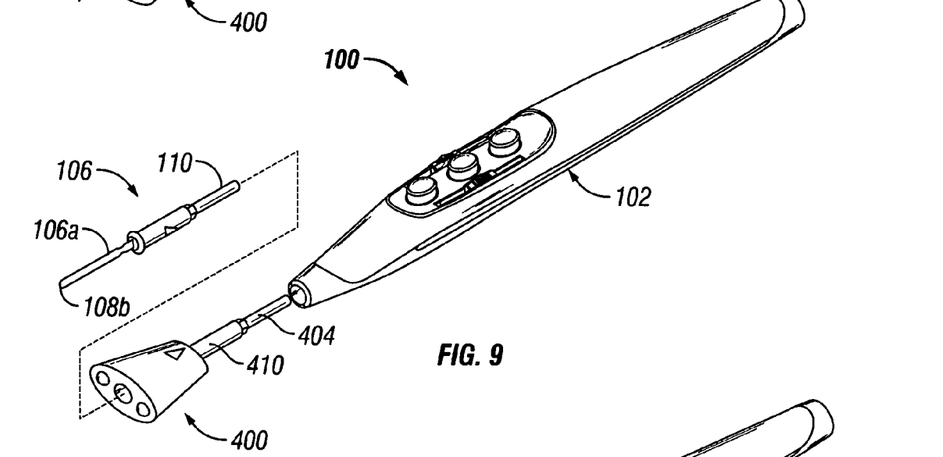
FIG. 9 is a perspective view of the electrosurgical pencil, LED adapter, and a needle electrode.
Figure 10:
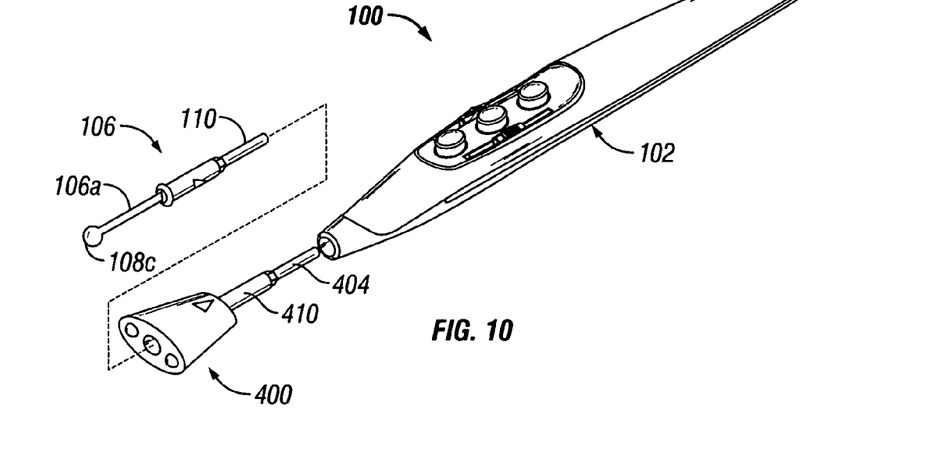
FIG. 10 is a perspective view of the electrosurgical pencil, LED adapter, and a ball electrode.
Figures 11, 12, 13:
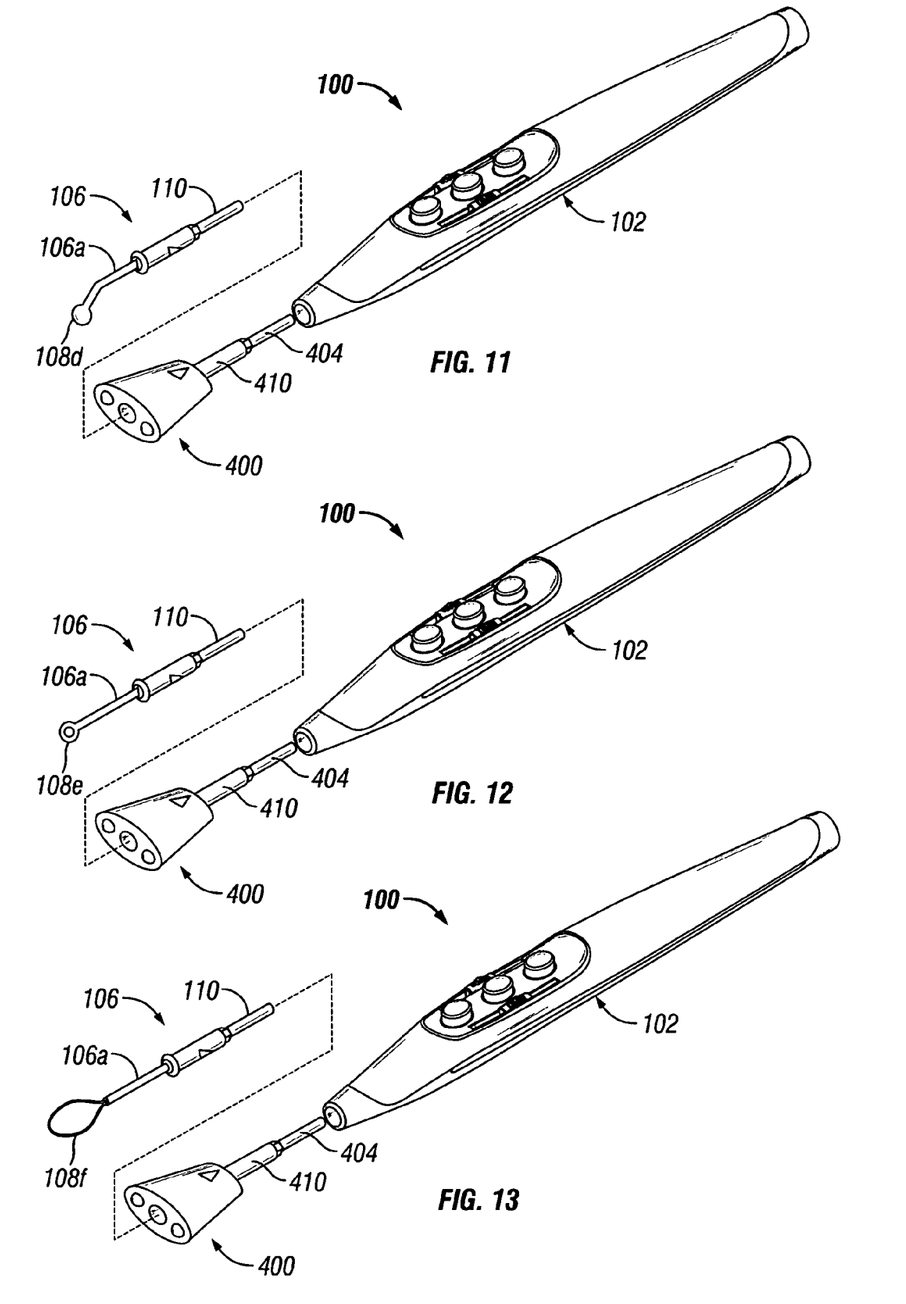
FIG. 11 is a perspective view of the electrosurgical pencil, LED adapter, and a angled ball electrode.
FIG. 12 is a perspective view of the electrosurgical pencil, LED adapter, and a loop electrode.
FIG. 13 is a perspective view of the electrosurgical pencil, LED adapter, and an conization electrode.

As illustrated in FIG. 7, it is also envisioned, LED adapter 400 may be configured to have LEDs 418 and 420 to emit at least one intermittent pattern relating to the operating status of electrosurgical pencil 100. For example, when a surgeon is performing a surgical procedure or upon termination of the procedure, LED 418 and/or 420 may display an intermittent pattern, e.g., blink, in such a manner to indicate to the surgeon that a certain procedure has ended.

It is also envisioned that LED adapter 400 may be configured to have LEDs 418 and/or 420 display an intermittent pattern in the event electrosurgical pencil 100 has detected an instrument malfunction. For example, LED adapter may be configured to enable LED 418 to display a green color and also to display an intermittent pattern, indicating that surgical instrument 100 is ready for operation. Alternatively, LED adapter may be configured to display a red color and/or display an intermittent pattern indicating that either there is a malfunction with surgical instrument system 10 and/or a certain operational procedure has ended or should be ended.

It is also envisioned that LED adapter 400 may be configured to have one LED display a "white" light or a suitable color of light for illuminating a surgical area, and any of the other LEDs display an indicator light color, e.g., red, green, yellow, or any suitable color for a certain situation or event. In this manner, there is both an indication LED and an illuminating LED on the same LED adapter 400.

As depicted in FIGS. 4-9, the distal end 108 of electrode 106 may be configured to include different shapes for different types of surgical procedures, i.e., blade electrode 108a, needle electrode 108b, ball electrode 108c, angled ball electrode 108d, loop electrode 108e, and conization electrode 108f.

It is contemplated that electrocautery blade 106 may be fabricated from a conductive type material, such as, for example, stainless steel or may be coated with an electrically conductive material.

Although the subject apparatus has been described with respect to the embodiments, it will be readily apparent, to those having ordinary skill in the art to which it appertains, that changes and modifications may be made thereto without departing from the spirit or scope of the subject apparatus.

What is claimed is:

1. An electrosurgical instrument, comprising:
   a housing having a distal end and a proximal end;
   an adapter having a proximal end including a collar configured to engage the distal end of the housing, and a distal end including a coupling interface, the adapter including at least one light source disposed therein, the light source adapted to connect to an electrosurgical energy source to emit light from the adapter; and
   at least one end effector having a proximal end configured to selectively engage the coupling interface on the distal end of the adapter and adapted to connect to the electrosurgical energy source, wherein the adapter is electrically coupled to the electrosurgical instrument, and the at least one end effector is electrically coupled to the electrosurgical instrument through the adapter.

2. The electrosurgical instrument according to claim 1, wherein the housing includes at least one switch that activates the end effector or the light source.

3. The electrosurgical instrument according to claim 2, wherein the switch simultaneously activates the light source and the end effector.

4. The electrosurgical instrument according to claim 1, wherein the light source includes at least one light-emitting diode.

5. The electrosurgical instrument according to claim 4, further comprising at least one switch that selectively activates at least one of the light-emitting diode and the end effector.

6. The electrosurgical instrument according to claim 1, wherein the light source is selectively activatable by a footswitch.

7. The electrosurgical instrument according to claim 1, wherein the adapter emits at least one color.

8. The electrosurgical instrument according to claim 1, wherein the adapter emits a plurality of colors.

9. The electrosurgical instrument according to claim 1, wherein the adapter emits light having an intermittent pattern.

10. The electrosurgical instrument according to claim 1, wherein the adapter simultaneously emits at least one intermittent pattern and at least one color.

11. The electrosurgical instrument according to claim 1, wherein the adapter includes a mechanical interface that selectively engages the end effector.

12. The electrosurgical instrument according to claim 1, wherein the electrosurgical instrument is an electrosurgical pencil, an electrosurgical scalpel, an electrosurgical forceps, or an electrosurgical probe.

13. The electrosurgical instrument according to claim 1, wherein a distal end of the end effector is configured to include the shape of a blade electrode, a needle electrode, a ball electrode, a angled ball electrode, a loop electrode, or a conization electrode.

14. An electrosurgical system, comprising:
an electrosurgical generator;
an electrosurgical instrument selectively connectable to the electrosurgical generator, the electrosurgical instrument including:
a housing having a distal end and a proximal end;
a light-emitting diode adapter having a proximal end including a collar configured to engage the distal end of the housing, and a distal end including a coupling interface, the light-emitting diode adapter including at least one light-emitting diode disposed therein, the light-emitting diode adapted to connect to an electrosurgical energy source and being selectively activatable to emit light from the adapter; and
at least one end effector having a proximal end configured to selectively engage the coupling interface on the distal end of the light-emitting diode adapter and adapted to connect to the electrosurgical energy source,
wherein the light-emitting diode adapter is electrically coupled to the electrosurgical instrument, and the at the one end effector is electrically coupled to the electrosurgical instrument through the light-emitting diode adapter.

* * * * *